United States Patent [19]

Guillou et al.

[11] Patent Number: Plant 7,720

[45] Date of Patent: Nov. 26, 1991

[54] VARIETY OF GERANIUM NAMED MONIQUE

[75] Inventors: Jacques Guillou; Bernard Guillou; Maurice Guillou, all of Saint-Malo, France

[73] Assignee: Etablissement Guillou Freres Jacques, Bernard et Maurice, Saint-Malo, France

[21] Appl. No.: 572,441

[22] Filed: Aug. 27, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new and distinct Geranium variety provides a new delicate lavender-pink bloom color and improved cutting production. The new variety has improved rooting capabilities and is more heat tolerant and resistant to shatter when compared to presently available commercial varieties.

1 Drawing Sheet

BACKGROUND OF THE INVENTION

The present invention comprises a new and distinct cultivar of the *Pelargonium*×*peltatum* known by the varietal name Monique (Oglevee No. 7031, French No. 424, Guisanfin). The new variety was discovered in a selective breeding program by Messrs. Jacques, Maurice and Bernard Guillou. The new variety is a selection from a crossing of No. 85 by No. 3.

The new cultivar was discovered in July 1988 at 55 rue Godard; 35400 Saint-Malo, France, was first asexually reproduced by cuttings during 1988 at Saint-Malo, France and more recently has been repeatedly asexually reproduced by cuttings at Oglevee Ltd. in Connellsville, Pa. It has been found to retain its distinctive characteristics through successive propagations.

The new cultivar when grown in a glass greenhouse in Connellsville, Pa. using full light 60° F. (night), 68° F. (day), and 71° F. (vent) and grown in a soilless media with constant fertilizer at 200 to 250 parts per million of nitrogen and potassium has a response time from a rooted cutting to a flowering plant in a 10 centimeter pot of 6 weeks.

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Pa. Plants were started as rooted cuttings which were potted on Aug. 1, 1989 and flowered on Sept. 15, 1989. The plant histories were taken on plants blossomed under full light in a greenhouse and color readings were taken indoors under 200–220 foot candles of cool, white fluorescent light. Color references are primarily to the R.H.S. Colour Chart of The Royal Horticultural Society of London.

THE PLANT

Classification:

*Botanical.*—*Pelargonium*×*peltatum.*

*Commercial.*—Ivy Geranium.

Form: Cascading mound habit.

Height: 18 cm above media surface.

Growth: Free and early flowering, free branching, upright mound habit with cascading side growth.

Strength: Has an upright mound habit while allowing outer branches to cascade over the sides of the pot.

Foliage: Stalk leaf attachment, little or no zone present.

Leaves:

*Size.*—5–10.5 cm.

*Shape.*—Reniform; cordate base.

*Margin.*—Pedately lobed.

*Texture.*—Leathery, coarsely haired, slightly reflective.

*Color.*—Top: Green Group 137B. Bottom: Green Group 137C.

*Ribs and veins.*—Venation palmate; Color Yellow-Green Group 146B.

Petioles: 2.5–5 cm, Yellow-Green Group 146B.

Stem:

*Color.*—Yellow-Green Group 146B.

*Internodes.*—2–6 cm in length.

THE BUD

Shape: Elliptical, upright.

Size: 1.0–2.5 cm across.

INFLORESCENCE

Blooming habit: Continuous and upright; early, some shattering present.

Size: 6.5–8.5 cm when fully open.

Borne: Florets on pedical, pedicel on peduncle; umbel 4.5–8.5 cm above foliage canopy.

Florets:

*Form.*—Flat to slightly cupped.

*Color.*—Top: Red-Purple Group 68A. Bottom: Red-Purple Group 68C.

*Petals.*—13–17 in number; separate; not united; obovate.

*Size.*—4.5–5.5 cm across when fully opened.

*Texture and appearance.*—Smooth; from a distance the color appears a delicate lavender-pink with a touch of maroon streaking near the center.

Petaloids:

*Quantity.*—Varies from 0–4.

*Shape.*—Elongated, twisted.

*Color.*—White at base to Red-Purple Group 67C near the tip.

Pedicel:

*Length.*—1.5–2.5 cm in length.

*Color.*—Yellow-Green Group 146C.

Peduncle: Arises from node opposite leaf petiole.

*Length.*—6–13.5 cm.

*Color.*—Yellow-Green Group 146B.

Disease resistance: Not known.

Lasting quality: The double blossoms tend to shatter less than the ivy geraniums now available.

REPRODUCTIVE ORGANS

Stamens:

*Anthers.*—Approximately 3.0 mm in length.

*Filaments.*—9.0 to 10 mm in lengths; white to a light pink.

*Pollen.*—Golden brown.

Pistils:

*Number.*—One; 5 to 6 parted.

*Length.*—9–11 mm.

*Stigma.*—5 or 6 parted; Red-Purple.

*Style.*—4 mm in length.

Ovaries: Superior; pale green; very pubescent; 4–5 mm in length; 2–3 mm wide.

Fruit: None observed.

This new variety provides not only a new and distinct bloom color of a delicate lavender-pink but also an improved cutting production. The branching habit provides many more cuttings than existing varieties and the ease of rooting has greatly improved. This variety is also more heat tolerant and more resistant to shatter than existing varieties.

I claim:

1. A new and distinct ivy Geranium, as shown and described herein.

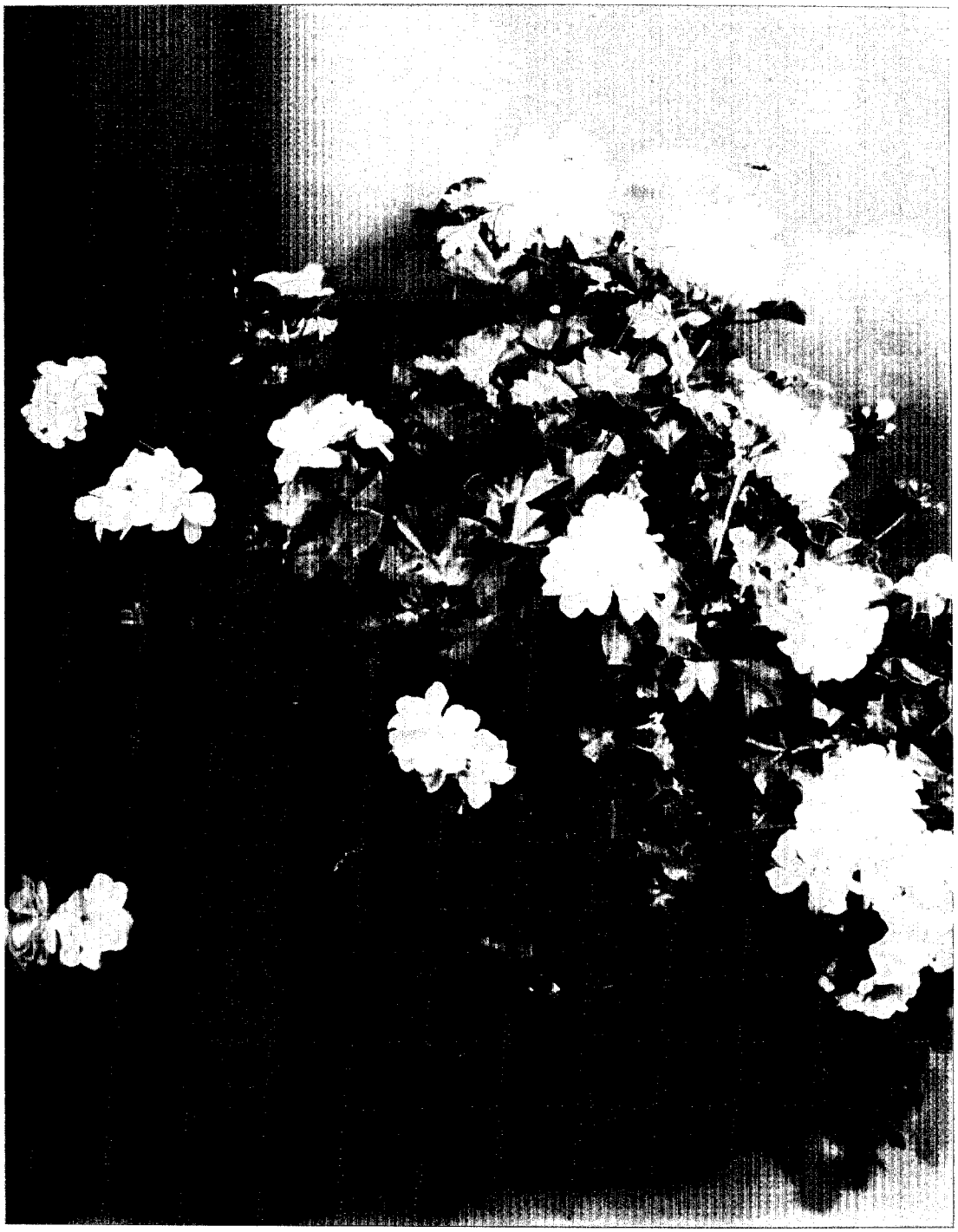

* * * * *